United States Patent [19]

Bridges et al.

[11] Patent Number: 4,589,729
[45] Date of Patent: May 20, 1986

[54] APPARATUS COMPRISING AN ARTICULATED ARM RADIATION GUIDE

[75] Inventors: Thomas J. Bridges, Holmdel; Albert R. Strnad, Colts Neck, both of N.J.

[73] Assignee: AT&T Bell Laboratories, Murray Hill, N.J.

[21] Appl. No.: 652,412

[22] Filed: Sep. 19, 1984

Related U.S. Application Data

[63] Continuation of Ser. No. 338,871, Jan. 12, 1982, abandoned.

[51] Int. Cl.⁴ ................................................. G02B 6/20
[52] U.S. Cl. ................................................... 350/96.32
[58] Field of Search ..................................... 350/96.32

[56] References Cited

U.S. PATENT DOCUMENTS

| | | | |
|---|---|---|---|
| 3,386,043 | 5/1968 | Marcatili | 330/4.3 |
| 3,913,582 | 10/1975 | Sharon | 128/303.1 |
| 4,122,853 | 10/1978 | Smith | 128/303.1 |

*Primary Examiner*—William L. Sikes
*Assistant Examiner*—Robert E. Wise
*Attorney, Agent, or Firm*—Eugen E. Pacher

[57] ABSTRACT

Articulated arm for guiding infrared radiation, with preferred wavelength between about 1 μm and about 100 μm, from a typically stationary radiation source to a moving or movable target. The inventive arm comprises hollow waveguides of the Marcatili-Schmeltzer type, with preferred bore diameter between about 50 and about 200 wavelengths of the radiation to be guided in the bore. Preferred waveguides consist of glass or quartz tubes of cylindrical cross section. The waveguides are typically held coaxially inside straight tubular members, the members being connected movably in end-to-end fashion. Beam direction altering means, for instance, reflecting means such as plane mirrors, serve to direct the radiation from the output end of one waveguide into the input end of the next waveguide. The articulated arm according to the invention typically is mode preserving, e.g., single mode radiation remains single mode, has high pointing accuracy, i.e., the direction of the output beam is substantially constant with respect to the axis of the output segment of the arm regardless of the spatial position or configuration of the arm. The arm can be designed to be mechanically light and higly maneuverable, and can be used in conjunction with a variety of output devices or probes. An exemplary probe useful, e.g., in transvitreal coagulation of retinal vessels, comprises hollow dielectric waveguides, including a tapered waveguide section. In addition to use in eye surgery and other surgical procedures, the inventive arm can advantageously be applied in such industrial processes as welding, soldering, cutting, annealing, scribing, drilling, and resistor trimming with infrared radiation.

9 Claims, 5 Drawing Figures

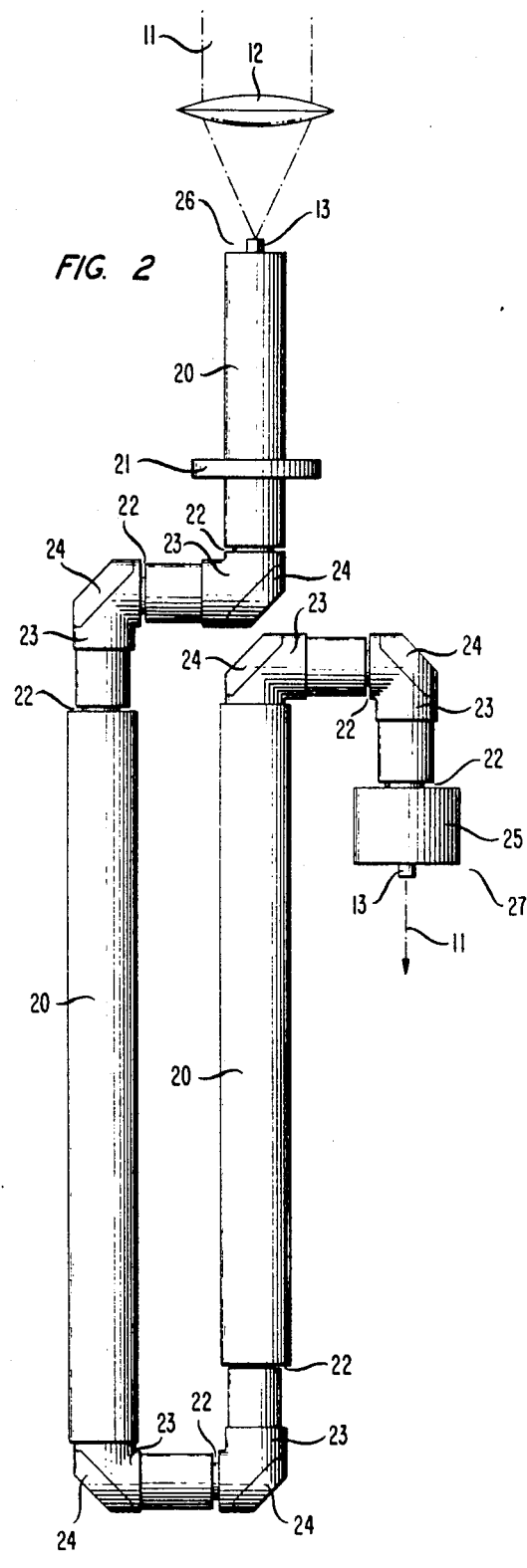
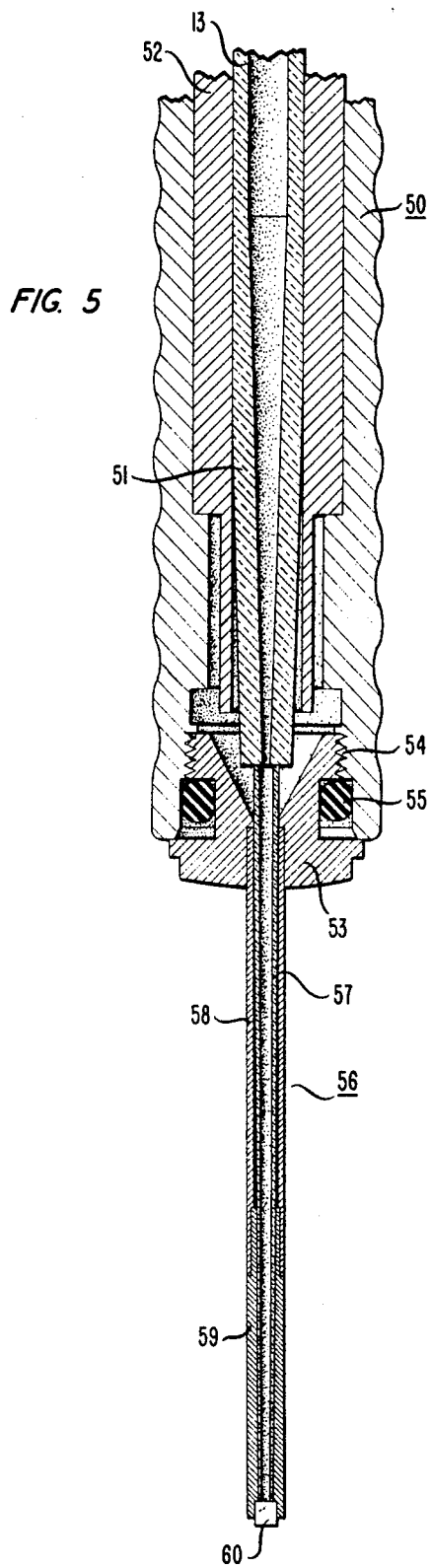

APPARATUS COMPRISING AN ARTICULATED ARM RADIATION GUIDE

This application is a continuation, of application Ser. No. 338,871, filed Jan. 12, 1982.

FIELD OF THE INVENTION

This invention pertains to an articulated arm for guiding radiation, especially infrared radiation.

BACKGROUND OF THE INVENTION

Laser radiation, e.g., 10.6 μm infrared (IR) radiation from $CO_2$ lasers, has found numerous applications in industry as well as in medicine. Among uses in industry are welding, soldering, cutting, laser annealing, scribing and drilling of substrates, and trimming of resistors. In medicine, typical applications of IR laser radiation are in ophthalmic retinal photocoagulation, and in dermatological, laryngological, and gynecological surgery.

The provision of a flexible path for IR radiation between the source and a variably positioned target has proved a difficult problem, and many solutions therefor have been proposed. Among such solutions are IR transmitting fibers, flexible metal waveguides, and conventional articulated arms.

IR-transmitting fiberguides are known in the art. For instance, D. A. Pinnow et al, *Applied Physics Letters*, Vol. 33(1), pp. 28-29, 1978 disclose polycrystalline thallium bromo-iodide and thallium bromide fibers which, according to these authors, have transmission loss and power handling capability satisfactory for image relay applications and surgical studies. However, the disclosed fibers are mechanically fragile, and for this and other reasons require a protective cladding. The above authors teach that the polycrystalline cores are inserted into a loose-fitting polymer cladding, which serves both as a means for optical confinement of the guided modes and as a means for mechanical protection of the fiber. However, it has been found that fibers of such construction lack mechanical strength. T. Hidaka et al, *Journal of Applied Physics*, Vol. 52(7), pp. 4467-4471, 1981. A medical laser instrument incorporating IR-transmitting fiber is disclosed in U.S. Pat. No. 4,170,997, issued Oct. 16, 1979 to D. A. Pinnow and A. L. Gentile.

In addition to the already mentioned fragility of the above described fiber, such fibers have further disadvantageous properties. In particular, single mode radiation from a laser coupled into such fiber typically rapidly degrades into multiple mode radiation, whose output pattern changes in form as the radiation path is changed. This degradation considerably reduces the maximum output energy density that can be obtained, and thus diminishes the utility of an IR laser device for many of the above-cited applications, since these typically require achievement of high energy density over a very small target area.

The use of a flexible, hollow metal waveguide for providing a radiation path between an IR radiation source and a variably positioned target was proposed by E. Garmire et al, *Applied Physics Letters*, Vol. 34(1), pp. 35-37, 1979. Although such guides can be constructed with sufficient mechanical stability, they typically also result in degradation of single mode radiation into multiple mode form, and thus suffer also from the above described shortcoming.

The use of articulated arms of conventional design as means for providing a flexible radiation path for IR laser radiation has been frequently disclosed. See, for instance, U.S. Pat. No. 3,658,406, issued Apr. 25, 1972 to N. Karube and Y. Morita; U.S. Pat. No. 3,913,582, issued Oct. 21, 1975, to U. Sharon; and U.S. Pat. No. 4,122,853, issued Oct. 31, 1978 to M. R. Smith. Articulated arms of conventional design consist of movably connected straight sections of, e.g., metal tubing, through whose bore a beam of unguided radiation can travel axially. The input beam diameter is typically considerably less than the bore diameter, but the beam diameter increases with increasing propagation distance due to diffraction spreading. Means for changing the propagation direction of the beam are placed at the junctions between adjacent straight sections of tubing, thus allowing maintenance of the axial propagation of the beam through a multiplesegment arm. Typical beam direction altering means are mirrors or prisms.

Single mode IR radiation launched into an articulated arm of conventional design typically remains single mode. However, unless the input beam is launched precisely on axis, and unless the arm is constructed to very close tolerances, such that the beam remains on axis regardless of configuration and orientation of the arm, the output beam will deviate from the axial direction of the output segment, and wander in a complicated manner as the arm is manipulated, i.e., such arms typically have low pointing accuracy. By "pointing accuracy," we mean herein the closeness of the direction of the output beam to the axis of the output segment of the arm, and "low" pointing accuracy refers to substantial beam deviation from the tube axis, typically in excess of about 1 degree. Since the applications of high intensity IR laser radiation typically require that the beam energy be directed to a predetermined and generally very small target region, typically much less than 1 $mm^2$, it is clear that low pointing accuracy constitutes a considerable drawback in a device for conveying the radiation to the target. In addition to having low pointing accuracy, articulated arms of conventional design typically also are large and cumbersome, requiring counter-weighting to permit precise control of the arm without application of substantial force, as required, for instance, for application in eye surgery.

The prior art means for providing a flexible radiation path between an IR laser source and a moving or movable target thus have shortcomings that make it difficult to realize the full potential of IR radiation in industrial and medical applications, and a radiation delivery system not subject to these shortcomings would inter alia be of considerable commercial interest.

SUMMARY OF THE INVENTION

The invention comprises means for guiding IR radiation from a source of that radiation to a moving or movable target. In particular, the invention comprises an articulated arm in which the radiation is guided in the straight segments of the arm, i.e., between successive changes in propagation direction, by means of hollow, substantially straight waveguides of the Marcatili-Schmeltzer type. Articulated arm according to the invention typically are mode-preserving, and can be constructed to be light-weight and highly maneuverable. Mode preservation implies, for instance, that single mode input radiation remains single mode. Such single mode output radiation of the inventive articulated arm can typically be focused to a near diffraction-limited spot size. Articulated arms according to the invention typically can have high pointing accuracy, allowing confident and accurate positioning of the output port of the beam-delivery means with respect to the intended target area, regardless of radiation path configuration. Articulated arms according to the invention thus can deliver high intensity radiation into a well-defined small target region.

Although substantially straight sections of either metallic or dielectric hollow waveguides can, in principle, be used in inventive articulated arms, we have found that such dielectric guides that are transparent at visible wavelengths offer advantages and are therefore preferred. In particular, such transparent guides can be used to deliver, in addition to the IR radiation propagating in the bore, visible target-illuminating radiation or pointing radiation to the target area, with the visible radiation travelling in the waveguide wall as well as the waveguide bore.

Articulated arms according to the invention can be used with a variety of radiation output means. We will refer herein to such output means as "probes". A particular probe incorporating a tapered dielectric waveguide section can be advantageously used, for instance, in eye surgery, e.g., in transvitreal coagulation of retinal vessels.

BRIEF DESCRIPTION OF THE DRAWINGS

FIG. 2 schematically shows the construction of a particular embodiment of the inventive articulated arm;

FIG. 5 schematically shows in cross-sectional view details of the construction of a probe that utilizes a tapered dielectric waveguide.

DETAILED DESCRIPTION

Figure 1:
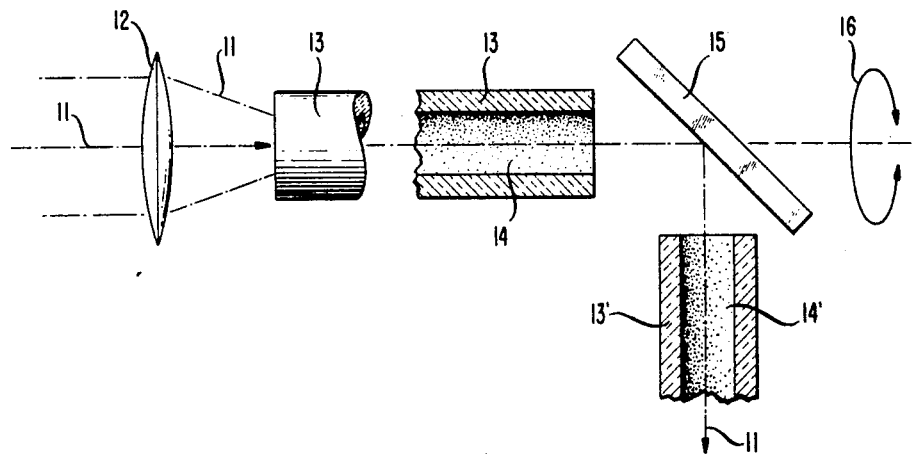
FIG. 1 is a schematic representation of the principle underlying the inventive arm.

Use of hollow waveguides of the Marcatili-Schmeltzer type (see for instance E. A. J. Marcatili and R. A. Schmeltzer, *The Bell System Technical Journal*, Vol. 43, pp. 1783-1809, 1964, incorporated herein by reference) permits construction of a compact and highly movable articulated arm for guiding IR radiation (by "IR radiation" we mean herein radiation with wavelength between about 1 $\mu$m and about 1000 $\mu$m, preferably not substantially exceeding 100 $\mu$m) from a typically stationary radiation source to a typically moving or movable target. Use of such waveguides typically results in preservation of the mode structure of the radiation, and thus in improved available maximum output energy density, and furthermore results in high pointing accuracy, that is to say, articulated arms according to the invention typically are far less affected by initial launch conditions of the input radiation and lack of accuracy of construction of the arm than prior art articulated arms. Incorporation of Marcatili-Schmeltzer type hollow waveguides into articulated arms for guiding IR radiation thus eliminates or substantially reduces shortcomings associated with prior art articulated arms.

The above indicated wavelength limits are due not to any fundamental properties of infrared radiation or of the waveguides, but instead are suggested inter alia by design considerations. As will be pointed out below, the preferred range of waveguide inner diameters is from about 50 to about 200 wavelengths of the guided radiation. Thus, for 100 $\mu$m radiation a preferred waveguide could have an inner diameter of about 5 mm or more. Waveguides of substantially larger bore would be bulky and thus inconvenient to use. And for wavelengths substantially in excess of 100 $\mu$m use of conventional metallic waveguides becomes possible, and would be preferred for wavelengths of 1000 $\mu$m and above. Similarly, for wavelengths of about 1 $\mu$m or less flexible optical fiberguides are available that could conveniently be used.

Marcatili-Schmeltzer type waveguides carry radiation in the hollow bore of a dielectric or metal tube. (E. A. J. Marcatili and R. A. Schmeltzer, op.cit., and U.S. Pat. No. 3,386,043, issued May 28, 1968 to E. A. J. Marcatili and R. A. Schmeltzer, for "Dielectric Waveguide, Maser Amplifier and Oscillator"). Such waveguides are well known in the art, and can be constructed by conventional and well known methods. Although the use of hollow metallic waveguides is possible in articulated arms according to the invention, and may in certain cases be advantageous, the use of dielectric waveguides typically offers certain advantages, as will be pointed out below, and we will substantially limit our discussion herein to arms using dielectric waveguides.

The dielectric in Marcatili-Schmeltzer type waveguides need not be transparent to the radiation being guided. The guiding mechanism can be thought of as a continual glancing-angle Fresnel reflection from the waveguide walls. This reflection is not total, but very close to 100 percent for shallow incident angles of the radiation. According to Marcatili and Schmeltzer (op. cit.), the lowest loss mode of a dielectric waveguide of circular cross section is a mode designated $EH_{11}$, which has an energy density that monotonically decreases towards the waveguide wall from its maximum on the waveguide axis, and use of this mode has been found advantageous by us. Considerable latitude exists in the choice of waveguide inner diameter (ID), but a preferred range of diameter size is from about 50 to about 200 wavelengths of the radiation to be guided. For radiation of about 10 $\mu$m wavelength, this corresponds to a bore diameter between about 0.5 mm and about 2 mm. The choice of bore diameter is typically affected by radiation loss considerations, since such loss increases with decreasing diameter. On the other hand, any curvature in the guide introduces radiation loss which increases with bore diameter. We find that the above-disclosed preferred range of bore diameters, i.e., between about 50 and 200 wavelengths, approximately encompasses those waveguide sizes that are large enough to give low loss but still retain adequate guiding such that the straightness of the guide is not an important design factor.

Since the dielectric of the waveguide need not be transparent to the guided radiation, glass or fused quartz tubing, which is readily available with precision circular bore of the appropriate size, can be used to guide IR radiation, and such tubing can advantageously be used in articulated arms according to the invention. Glass or quartz waveguides, or other waveguides transparent in the visible, can, in addition to guiding the IR radiation, form light pipes for carrying visible radiation through the arm. This radiation can be used for illumination of the target region, or for aiming of the output probe.

In waveguides according to the invention, the output radiation of an appropriate source, typically an IR laser such as a $CO_2$ laser, is coupled into a nominally straight section of waveguide and propagates therethrough until encountering beam-direction-altering means, which serve to couple the radiation into another similar waveguide section. This situation is schematically illustrated in FIG. 1. The beam of radiation 11 is directed into the input port of dielectric waveguide 13 by means of lens 12, and the radiation propagates through bore 14 of the waveguide until encountering beam-direction-altering means, exemplified through mirror 15, oriented so as to direct the radiation into the bore 14' at the input end of another dielectric waveguide 13'. The focal length of the lens can be chosen to match the input radiation, which advantageously has a Gaussian profile, to the guided radiation, preferably the $EH_{11}$ mode. Short gaps in the guided path can be tolerated, and typically cause only small radiation loss. A simple arrangement of waveguides and beam-direction-altering means is therefore possible. This is also schematically indicated in FIG. 1, where the turning mirror is shown not to be in direct contact with the two waveguides. Direction-arrow 16 is used to indicate that waveguide 13' together with mirror 15 can be rotated about the axis of waveguide 13.

A specific embodiment of the articulated arm according to the invention is schematically shown in FIG. 2. A beam of radiation 11 is launched through lens 12 into dielectric waveguide 13 at the input end 26 of the articulated arm. The radiation is guided through three elongated straight segments 20 of the arm, is reflected by about 90 degrees at six corner sections 23, and emerges from the arm at output end 27. Seven movable joints 22 result in variability of the radiation path. In particular, joints 22 permit free rotation of cornerpieces 23, in which infrared-reflecting mirrors, not shown in this figure, are held in place by cornerplates 24, around the axis of the straight arm section movably attached to the respective cornerpiece. Connector means 25 permits attachment of beam output means, i.e., a probe, to the output side 27 of the articulated arm, and collar 21 constitutes part of the coupling mechanism for attaching the articulated arm to a radiation source.

Figure 3:
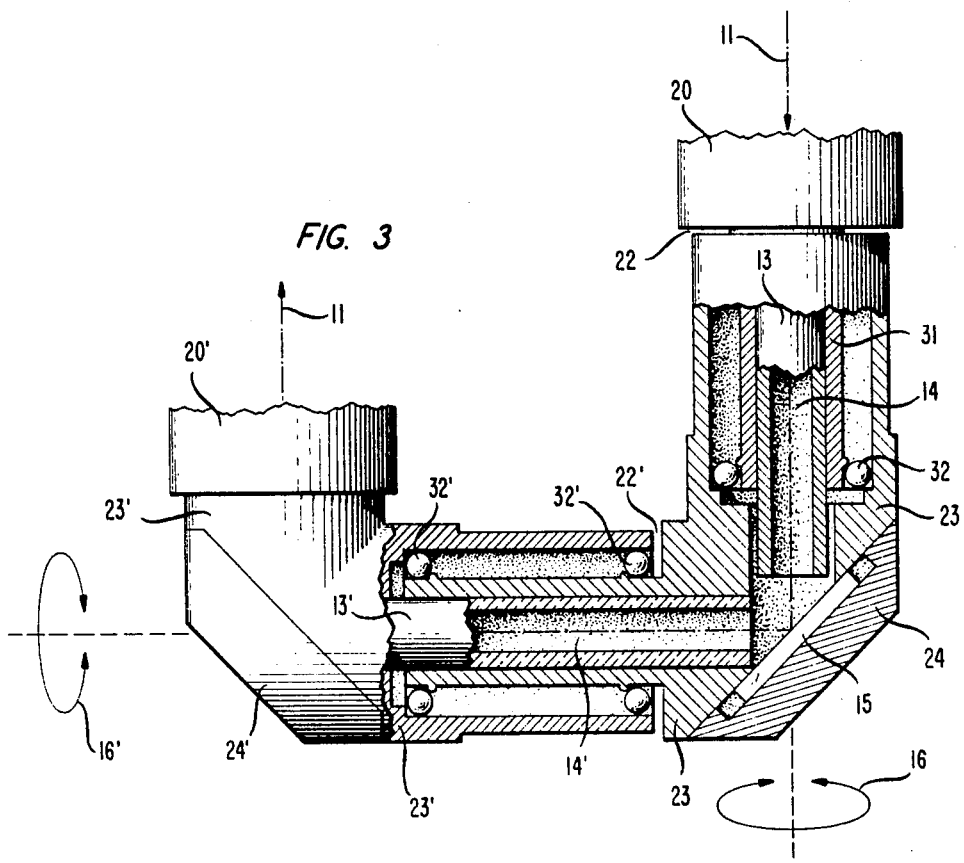
FIG. 3 schematically shows in partial cross-sectional view detail of the construction of a particular embodiment of the inventive arm.

FIG. 3 schematically shows in partial cross-section the construction of a corner section of the articulated arm according to the invention. The section comprises two corner pieces 23 and 23', and two rotatable connections 22 and 22'. Radiation 11 is guided through straight segment 20 of the articulated arm in bore 14 of waveguide 13. The waveguide is held in radially and axially fixed relationship with respect to arm segment 20 by means of support tube 31 and two precision ball bearings 32, only one of which is shown in FIG. 3. After exiting from waveguide 14 and propagating for a short distance through free space, the radiation is reflected at mirror 15 and redirected into bore 14' of waveguide 13', which is secured to corner piece 23. Corner piece 23', which is permanently joined, e.g. brazed, to straight arm segment 20' is maintained in radially and axially fixed relationship with respect to corner piece 23 by means of two ball bearings 32'. Radiation reflected by mirror 15 into waveguide bore 14' propagates through waveguide 13' and, after a further reflection by a mirror similar to 15 but not shown in FIG. 3, continues towards the output end of the articulated arm. The turning mirrors, e.g., mirror 15, are protected and held in place by means of cover plates such as 24 and 24'. Direction arrows 16 and 16' again indicate the rotational degree of freedom provided by the construction shown schematically in FIG. 3.

Figure 4:
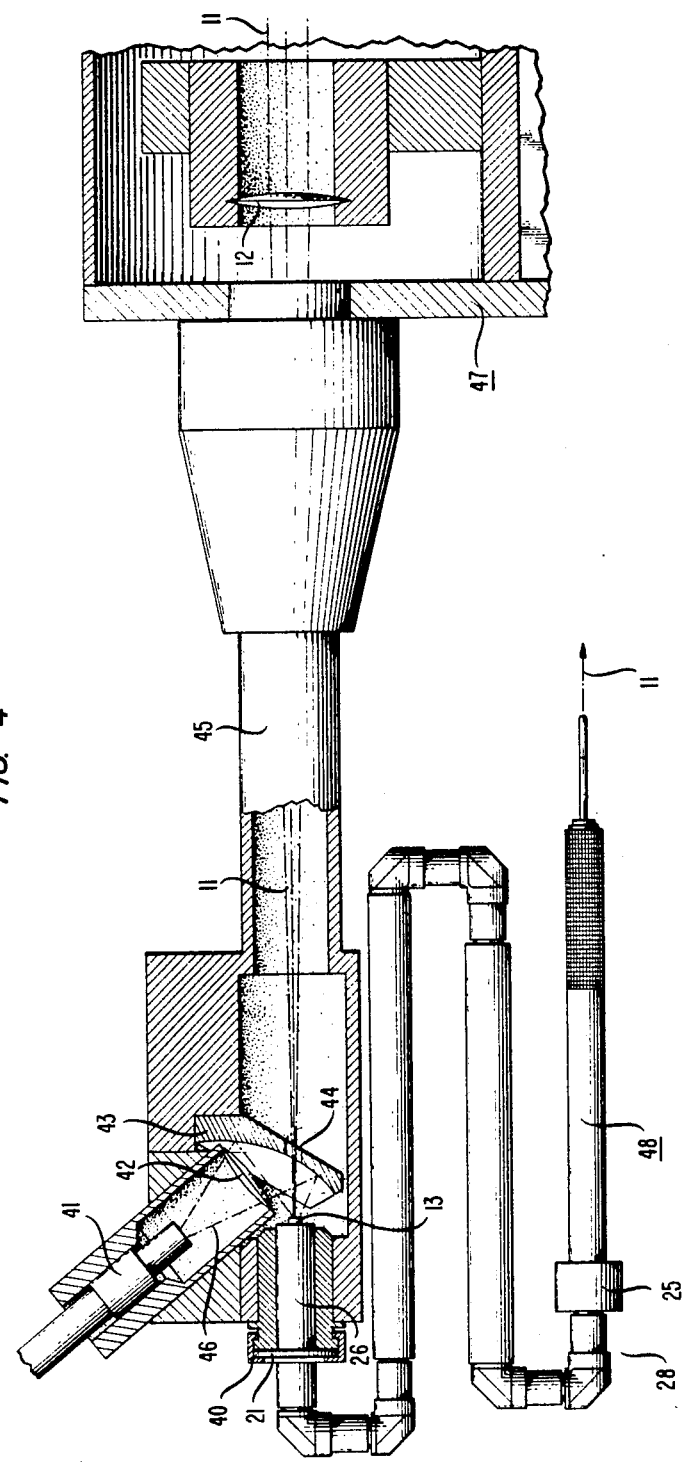
FIG. 4 schematically shows the construction of a particular embodiment including means for coupling the articulated arm to a laser source of IR radiation and to a source of illuminating visible radiation.

FIG. 4 schematically depicts an articulated arm according to the invention coupled to a source of IR radiation and a source of visible illuminating radiation, with an output probe attached to the output end of the articulated arm. Infrared radiation 11 is directed by means of lens 12 through aperture 44 onto waveguide 13 maintained in the input end 26 of the articulated arm. The articulated arm is attached to the radiation source by means of support tube 45 and housing 47. Collar 21 and threaded ring 40 permit interchangeability of the articulated arm. Visible light 46 from fiber optic light pipe 41 is focused by auxiliary lens 42 onto ellipsoidal mirror 43, and thereby directed onto dielectric waveguide 13, which carries the visible light both in the transparent waveguide wall as well as in the bore. Output means 48 are attached to the output end of the articulated arm 28 by means of connector 25.

FIG. 5 schematically shows in cross section the output end part of a probe according to the invention. In particular, the probe uses dielectric waveguides to conduct infrared radiation from the output end of an articulated arm to the probe tip. The mechanical coupling arrangement by which the probe is connected to the articulated arm is not shown in FIG. 5, since such schemes are well known in the art. Probe handle 50 contains an axial cylindrical bore in which dielectric waveguide 13 is maintained in fixed position by spacer tube 52. Tapered section 51 of the dielectric waveguide serves to feed the infrared radiation into a smaller diameter dielectric waveguide 57 inside composite probe tip 56. The composite probe tip comprises a stem 58 and a tip 59 securely joined to the stem. The stem, advantageously consisting of stainless steel, provides strength to the composite tip, and the tip section, for at least some applications advantageously consisting of silver, can form an anti-corrosion interface. Exit window 60 serves to seal the probe tip while transmitting both the IR radiation and visible radiation. The composite tip 56 is rigidly connected to ferrule 53, e.g., by means of a braze joint, and the ferrule attached to handle 50 by means of a threaded section 54, with O-ring 55 providing a hermetic seal.

The inventive articulated arm can be designed in a variety of ways, and used in conjunction with a variety of radiation sources and radiation-modifying optical and mechanical devices, for a variety of purposes. An exemplary apparatus, designed primarily for transvitreal coagulation of retinal vessels, will now be described.

Example: A Sylvania Model 948 $CO_2$ laser provides about 8W cw infrared radiation of 10.6 μm wavelength. A Sylvania Model 485 laser attenuator is used to control the beam power over about 2-95 percent of the laser output, and a Coherent Model 210 power meter serves to monitor the beam power. A mechanical shutter system, namely, a modified Uniblitz Model 114 LOAOZ5, used with Model 310 programmable actuator which controls opening time from about 50 msec to about 100 sec, directs in its closed position laser radiation via a mirror to the power meter, and in its open position transmits light to the delivery system. A coated zinc selenide focusing lens of 25.4 cm focal length in an adjustable mount serves to direct the infrared radiation onto the input side of the articulated arm, analogous to the manner shown in FIG. 4, and thereby to optically couple the laser radiation into the dielectric waveguide.

The exemplary articulated arm is closely analogous to the arm depicted schematically in FIGS. 2 and 3. The arm contains an input section of about 6 cm length, two cylindrical sections of approximately 13 cm length each, and three cylindrical sections of approximately 2 cm length each. These sections consist of stainless steel tubing, with an outer diameter of 10 mm. Dielectric waveguide sections are mounted coaxially inside the tube sections. The six turning mirrors used consist of about 1 mm thick highly polished silicon wafers, coated with silver and a transparent protective layer. Corner pieces move on precision ball bearings that allow free rotation of any movable segment with respect to the fixed segment attached thereto. With a total length of approximately 40 cm the arm can access any point within a sphere of about 80 cm diameter.

Fused quartz tubing of circular cross-section, with a precision 1.55 mm diameter bore, is used as the dielectric waveguide. We found that, for instance, a 13.9 cm length of such tubing has a transmission of about 93 percent, when used in conjunction with a 25.4 cm focal length lens that directs the radiation into the guide. We also found that small guide misalignments have a small effect on the transmission of radiation through the guide. In particular, when the tube was pivoted off axis around the input point by about $\frac{1}{2}$ degree, the transmission was found to drop only by approximately two percent.

The exemplary arm has a transmission at 10.6 $\mu$m of approximately 80 percent, and can transmit IR power at least up to about 5W cw without suffering damage. The radiation exiting from the output port of the exemplary arm is typically substantially single mode, and typically can be focused to a near diffraction limited spot.

We typically use the exemplary arm in conjunction with a work illumination system, analogous to the system shown in FIG. 4. Visible light from a 150W Quartz Halogen Illuminator (Dolan-Jenner Model 180) is guided by means of a fiber optic light pipe (Dolan-Jenner Model B436), and focused by an auxiliary lens (Dolan-Jenner LH759) onto an apertured ellipsoidal mirror that reflects the visible radiation into the bore and wall of the dielectric waveguide.

Output probes of a variety of designs can be attached to, and used with, articulated arms according to the invention. An exemplary device useful for, e.g., transvitreal coagulation of retinal vessels will now be described. The device or probe, closely analogous to the probe shown in FIG. 5, consists of a handle section and a detachable probe tip, with fused quartz waveguides used to guide IR radiation through the probe. In particular, a 96 mm long straight guide section having 1.55 mm diameter precision bore is followed by a 23 mm long section tapering uniformly from 1.55 mm to about 0.5 mm bore diameter. The end of the tapered section abuts against the input end of a 33 mm long, 0.8 mm ID waveguide section contained in a composite probe tip attached, in a hermetically sealed fashion, to the handle section of the probe. The probe tip is closed by means of a polished diamond window, sealed into the silver end section of the composite probe tip with silver bromide sealant. A diamond output window can have advantages, especially for probes used in applications such as laser ophthalmic surgery. In particular, a Type II diamond provides high transmission of $CO_2$ laser radiation, and high thermal conductivity. The diamond window surface remains essentially unaffected by the power densities of radiation of interest in this application, and by burning or evaporating target material. Burned-on layers of material are easily removed without damage to the window by scraping, and diamond is easily soldered to a silver probe tip with silver bromide, a highly insoluble nontoxic material having a melting point of 432° C.

In order to operate the exemplary system, support electronics and hardware, e.g., a laser power supply, switches, warning lights and the like, are required. However, such items are standard and their use well known to those skilled in the art, and need not be discussed in detail.

What is claimed is:

1. Apparatus comprising an articulated arm for guiding infrared radiation, the infrared radiation having a wavelength and a propagation direction, the articulated arm comprising
  (a) a multiplicity of substantially straight tube members including a first tube member and a second tube member, each tube member having an axis, an input end and an output end;
  (b) connecting means for movably connecting the output end of the first tube member to the input end of the second tube member, the first tube member being connected by the connecting means to the second tube member,
  (c) radiation propagation direction altering means,
  (d) means for attaching the articulated arm to infrared radiation generating means, and
  (e) means for attaching radiation output means to the articulated arm, Characterized in That the articulated arm further comprises
  (f) a multiplicity of tubular dielectric infrared radiation guiding means of the Marcatili-Schmeltzer type including first guiding means and second guiding means, the first and second guiding means each substantially consisting of dielectric material that is substantially transparent to at least some radiation in the visible part of the electromagnetic spectrum, and each having substantially circular cross section, with bore diameter between about 50 times and about 200 times the wavelength of the infrared radiation, the first guiding means being maintained substantially within the first tube member, and the second guiding means being maintained substantially within the second tube member, and
  (g) the propagation direction altering means comprise reflecting means adapted for directing at least a substantial part of infrared radiation incident thereon from the first guiding means into the bore of the second guiding means.

2. Apparatus comprising an articulated structure for guiding infrared electromagnetic radiation, the infrared radiation having a wavelength and a propagation direction, the articulated structure comprising
  (a) first hollow infrared radiation guiding means of the Marcatili-Schmeltzer type, to be referred to as the first guiding means, and second hollow infrared radiation guiding means of the Marcatili-Schmeltzer type, to be referred to as the second guiding means, the first and the second guiding mean each comprising dielectric material that is substantially transparent to at least some radiation in the visible part of the electromagnetic spectrum, and each having an axis, an input end, and an output end;

(b) means for supporting the first guiding means, the means to be referred as the first support means, and means for supporting the second guiding means, the means to be referred as the second support means, the second support means movably connected to the first support means; and (c) means for altering the propagation direction of the infrared radiation adapted for directing at least a part of the infrared radiation, after propagation of the infrared radiation through the first guiding means, into the second guiding means input end.

3. Apparatus of claim 2, wherein each of the first and second guiding means comprise a fused quartz tube having a bore diameter in he range 50 to 200 times the wavelength of the infrared radiation.

4. Apparatus of claim 3, wherein at least the first support means comprise a substantially straight tube member, with the first guiding means being maintained substantially within the tube member.

5. Apparatus of claim 4, further comprising first means for generating the infrared radiation, and means for attaching the articulated structure to the first means such that at least some of the infrared radiation generated by the first means will be directed into the bore of the input end of the first guiding means quartz tube.

6. Apparatus of claim 5, further comprising second means for generating radiation in the visible part of the electromagnetic spectrum, and means for directing at least some of the radiation generated by the second means into the first guiding means quartz tube.

7. Apparatus of claim 5, further comprising radiation output means, to be referred to as a probe, the probe comprising tubular infrared radiation guiding means of the Marcatili-Schmeltzer type, to be referred to as the probe guiding means, the probe guiding means comprising a fused quartz tube, the apparatus also comprising means for attaching the probe to the articulated structure such that at least some of the infrared radiation generated by the first means will be directed from the articulated structure into the probe guiding means.

8. Apparatus of claim 7, further comprising second means for generating radiation in the visible part of the electromagnetic spectrum, and means for coupling at least some of the radiation generated by the second means into the quartz tube of the probe guiding means.

9. Apparatus of claim 7, wherein the quartz tube of the probe guiding means comprises a tapered portion wherein the bore diameter decreases from a first diameter to a second diameter.

* * * * *